US011549125B2

(12) United States Patent
Li et al.

(10) Patent No.: US 11,549,125 B2
(45) Date of Patent: Jan. 10, 2023

(54) CLOSED-ENDED, LINEAR, DUPLEX ADENOASSOCIATED VIRUS DNA, AND USES THEREOF

(71) Applicant: THE USA, AS REPRESENTED BY THE SECRETARY, DEPT. OF HEALTH AND HUMAN SERVICES, Bethesda, MD (US)

(72) Inventors: Lina Li, Potomac, MD (US); Robert Kotin, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 82 days.

(21) Appl. No.: 16/637,152

(22) PCT Filed: Aug. 9, 2017

(86) PCT No.: PCT/US2017/046059
§ 371 (c)(1),
(2) Date: Feb. 6, 2020

(87) PCT Pub. No.: WO2019/032102
PCT Pub. Date: Feb. 14, 2019

(65) Prior Publication Data
US 2020/0270636 A1   Aug. 27, 2020

(51) Int. Cl.
*C12N 7/00* (2006.01)
*C12N 15/86* (2006.01)
(Continued)

(52) U.S. Cl.
CPC .............. *C12N 15/86* (2013.01); *A61K 35/76* (2013.01); *C12N 7/00* (2013.01); *C12N 15/11* (2013.01);
(Continued)

(58) Field of Classification Search
None
See application file for complete search history.

(56) References Cited

U.S. PATENT DOCUMENTS 7,271,002 B2    9/2007   Kotin et al.
2011/0003884 A1*  1/2011   Pugachev ............ A61K 39/145
                                                514/44 R
(Continued)

FOREIGN PATENT DOCUMENTS

EP         2412387          2/2012
WO    WO 2007/084773       7/2007
(Continued)

OTHER PUBLICATIONS

Merriam-Webster, "Devoid", found online at https://www.merriam-webster.com/dictionary/devoid (Year: 2021).*
(Continued)

*Primary Examiner* — M Franco G Salvoza
(74) *Attorney, Agent, or Firm* — Leydig, Voit & Mayer, Ltd.

(57) ABSTRACT

Closed-ended, linear, duplex (CELID) DNA molecules, recombinant AAV (rAAV), particles comprising CELID DNA, methods of making such molecules and particles, and therapeutic applications of such particles.

23 Claims, 1 Drawing Sheet

(51) Int. Cl.
    A61K 35/76      (2015.01)
    C12N 15/11      (2006.01)
(52) U.S. Cl.
    CPC ................ C12N 2310/532 (2013.01); C12N
              2750/14123 (2013.01); C12N 2750/14143
                                            (2013.01)

(56) References Cited

U.S. PATENT DOCUMENTS

| | | | |
|---|---|---|---|
| 2011/0262394 A1* | 10/2011 | Ramanathan | A61P 37/04 424/85.2 |
| 2014/0107186 A1 | 4/2014 | Garcia et al. | |
| 2017/0130245 A1* | 5/2017 | Kotin | C07K 14/005 |

FOREIGN PATENT DOCUMENTS

| WO | WO 2012/123430 | 9/2012 | |
|---|---|---|---|
| WO | WO-2015191508 A1 * | 12/2015 | C12N 15/86 |

OTHER PUBLICATIONS

Wu et al., "Effect of Genome Size on AAV Vector Packaging," Molecular Therapy, vol. 18, No. 1: 80-86 (Year: 2010).*

Choi et al. "The Effect of DNA-Dependent Protein Kinase on Adeno-Associated Virus Replication," PLOSOne, Dec. 2010, vol. 5, No. 12, e15073, 10 pages.

Hong et al. "In vitro replication of adeno-associated virus DNA," Proceedings of the National Academy of Sciences of the United States of America, May 1992, vol. 89, pp. 4673-4677.

Hong et al. "Intermediates of Adeno-Associated Virus DNA Replication In Vitro," Journal of Virology, Mar. 1994, vol. 68, No. 3, pp. 2011-2015.

Li et al. "Production and Characterization of Novel Recombinant Adeno-Associated Virus Replicative-Form Genomes: A Eukaryotic Source of DNA for Gene Transfer," PLOSOne, Aug. 2013, vol. 8, No. 8, e69879, 14 pages.

Li et al. "Closed-Ended Linear Dubplex AAV (celdAAV) DNA for Non-Viral Gene Transfer," Molecular Therapy, May 2012, vol. 20, Suppl. 1, p. S236.

Li et al. "High-Yield AAV Production Clonal SF9/ITR-GFP Stable Cell Lines Obtained from Spodoptera frugiperda Sf9 Cells," Molecular Therapy, May 2009, vol. 17, Suppl. 1, p. S272.

Mietzsch et al. "OneBac 2.0: Sf9 Cell Lines for Production of AAV1, AAV2, and AAV8 Vectors with Minimal Encapsidation of Foreign DNA," Human Gene Therapy Methods, Feb. 2017, vol. 28, No. 1, pp. 15-22.

Nahreini et al. "Cloning and integration of DNA fragments in human cells via the inverted terminal repeats of the adeno-associated virus 2 genome," Gene, 1992, vol. 119, pp. 265-272.

Ni et al. "In Vitro Replication of Adeno-Associated Virus DNA," Journal of Virology, Feb. 1994, vol. 68, No. 2, pp. 1128-1138.

Penaud-Budloo et al. "Accurate Identification and Quantification of DNA Species by Next-Generation Sequencing in Adeno-Associated Viral Vectors Produced in Insect Cells," Human Gene Therapy Methods, Jun. 2017, vol. 28, No. 3, pp. 148-162.

Samulski et al. "Targeted integration of adeno-associated virus (AAV) into human chromosome 19," The EMBO Journal, 1991, vol. 10, No. 12, pp. 3941-3950.

Snyder et al. "In Vitro Resolution of Covalently Joined AAV Chromosome Ends," Cell, Jan. 1990, vol. 60, pp. 105-113.

Urabe et al. "Scalable Generation of High-Titer Recombinant Adeno-Associated Virus Type 5 in Insect Cells," Journal of Virology, Feb. 2006, vol. 80, No. 4, pp. 1874-1885.

Yang et al. "Cellular Recombination Pathways and Viral Terminal Repeat Hairpin Structures Are Sufficient for Adeno-Associated Virus Integration In Vivo and In Vitro," Journal of Virology, Dec. 1997, vol. 71, No. 12, pp. 9231-9247.

Zhang et al. "Site-specific integration of CAR gene into Jurkat T cells with a linear close-ended AAV-based DNA vector for CAR-T engineering," Biotechnology Letters, Jun. 2016, vol. 38, No. 9, pp. 1423-1431.

International Preliminary Report on Patentability for International (PCT) Patent Application No. PCT/US2017/046059, dated Feb. 20, 2020 11 pages.

International Search Report and Written Opinion prepared by the European Patent Office dated Oct. 27, 2017, for International Application No. PCT/US2017/046059.

Karbowniczek et al., Doggybone™ DNA: an advanced platform for AAV production, Cell & Gene Therapy Insights, pp. 731-738 (published Nov. 16, 2017).

* cited by examiner

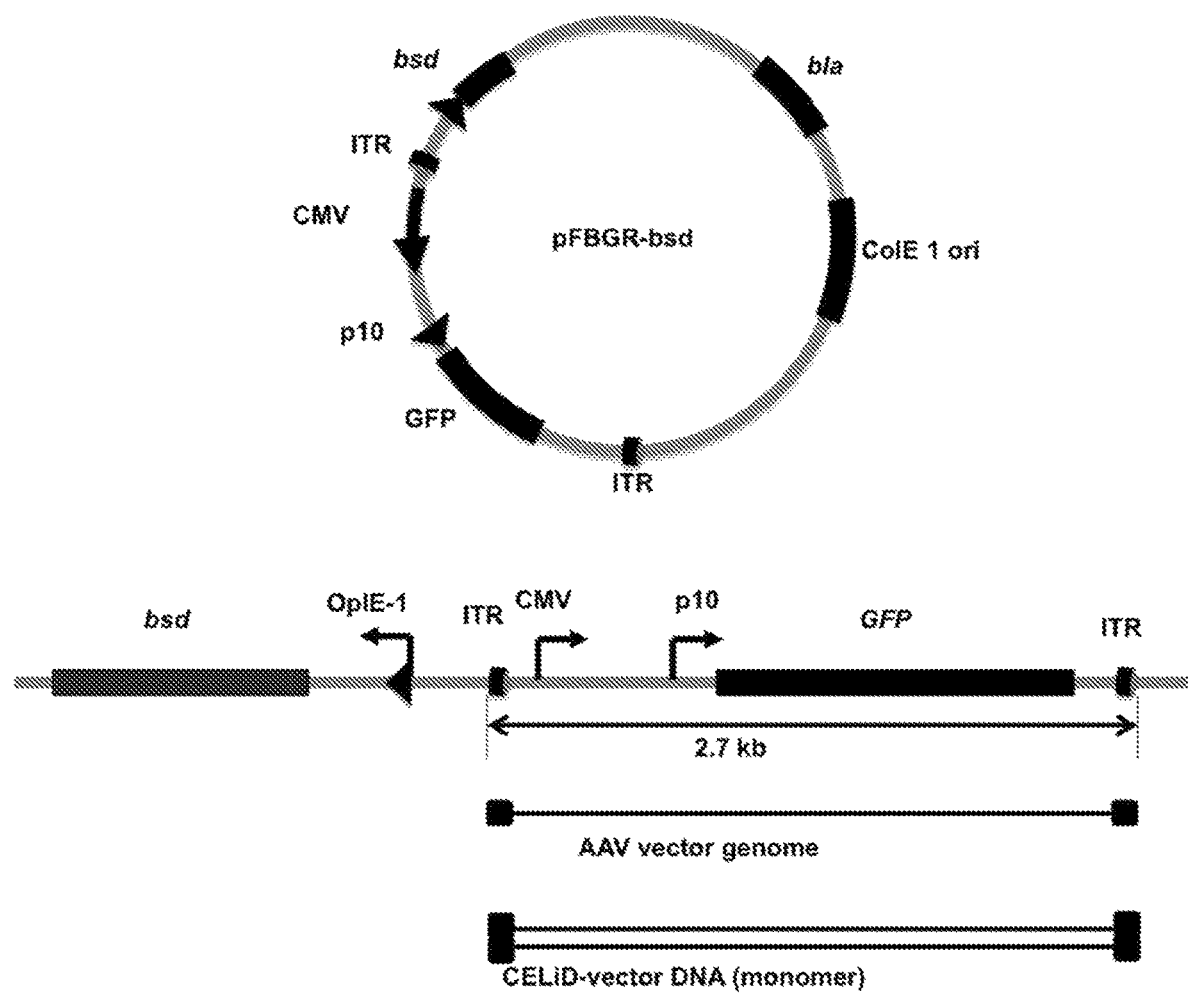

CLOSED-ENDED, LINEAR, DUPLEX ADENOASSOCIATED VIRUS DNA, AND USES THEREOF

CROSS REFERENCE TO RELATED APPLICATION

This application is a national stage application under 35 U.S.C. 371 of PCT Application No. PCT/US 2017/046059 having an international filing date of 9 Aug. 2017, which designated the United States, the disclosures of which is incorporated herein by reference in its entirety.

FIELD OF THE DISCLOSURE

This disclosure relates to the production of AAV vectors, recombinant AAV particles comprising such AAV vectors, and the therapeutic use of such vectors and recombinant AAV particles.

BACKGROUND

The delivery of therapeutic agents to individuals in need of treatment has historically been achieved either orally or by injection. While such administration is generally effective, it usually requires repeated administration, and results in systemic distribution, which is not always desirable. Moreover, although enzyme replacement therapies may remediate the loss of function caused by a genetic mutation, such treatments are typically restricted to alleviating symptoms, and do not address the underlying genetic defect.

A goal of modern medicine is to develop improved methods of treatment that require less frequent administration, that can be specifically targeted to organs and tissues, or metabolic or other pathways of illness, and/or that are suitable for treating the genetic defect underlying a genetic disorder or disease. One approach to achieving such treatment involves delivery of a heterologous DNA molecule into cells in a patient in need of such treatment. Once delivered, the heterologous DNA molecule can remain as an episome or extrachromosomal element in the nucleus, where it can be transcribed into RNA. The RNA may encode a protein, which can act within the cell, or which may be exported from the cell to act systemically, or in a paracrine, endocrine, or autocrine manner. The heterologous DNA molecule may also encode regulatory RNA, such as miRNA or shRNA. Alternatively, the heterologous DNA molecule can be inserted into the cellular genome through homologous DNA recombination (or repair), non-homologous end-joining, transposase-mediated recombination, site-directed nuclease (e.g., zinc-finger or TALEN), or RNA-guided methodologies (e.g. CRISPR/Cas9). Delivery of the heterologous DNA can be carried out using various methods, one of which includes the use of a viral vector. While many viral vectors are available, adeno-associated virus (AAV) vectors have become a favored vector among gene therapy researchers.

Vectors derived from AAV are particularly attractive for delivering genetic material because: 1. The vectors are incapable of autonomous replication, 2; the vectors can infect (transduce) a wide variety of non-dividing and dividing cell types; 3. the vectors can be systemically delivered to transduce liver, muscle, and brain; and, 4. the vectors can be administered locally to transduce photoreceptors or other cell types in the eye, intracranially to transduce specific regions of the brain, or intrathecally to transduce motor neurons and spinal neurons. Further, AAV vectors can be devoid of the virus structural genes, thereby eliminating some aspects of the natural host cell responses to virus infection. Moreover, wild-type AAVs have never been etiologically associated with any pathology in humans, and replication-deficient AAV vectors generally persist as episomes, thus limiting the risk of insertional mutagenesis or activation of oncogenes. In addition, AAV vectors can also be produced at high titer.

Adeno associated viruses (AAV) comprise the dependoparvovirus subfamily of the Parvoviridae. The dependoparvoviruses are distinct from the other members of this virus family by its dependence upon a helper virus for a productive infection. In the absence of a helper virus, in Rep-dependent process, AAV DNA has been shown to integrate in a locus specific manner into the q arm of human chromosome 19. The approximately 5 kb virion genome of AAV consists of a linear, single-stranded DNA molecule of either plus or minus polarity. Physically, the AAV particle is non-enveloped and the icosohedral capsid (T=1 symmetry) is approximately 20-25 nm in diameter. The genome of AAV contains three large open reading frames (ORFs): the left ORF, encoding non-structural replication (Rep) proteins (Rep78, Rep68, Rep52 and Rep40), which are involved in replication, gene regulation, encapsidation, and integration, and the right ORF, which encodes the structural capsid (Cap or VP) proteins, and the assembly activating protein (AAP) that is translated from a second ORF within the Cap ORF.

Flanking the AAV coding regions are two cis-acting nucleotide inverted terminal repeat (ITR) sequences, each of which are approximately 145 nucleotides in length. The ITRs contain interrupted palindromic sequences having the potential to fold into T-shaped hairpin structures, which serve as the origin of viral DNA replication. Within the ITR region, two elements have been described which are central to the function of the ITR: a GAGC repeat motif and the terminal resolution site RGTTGR (trs). The repeat motif has been shown to bind multimeric Rep 78 or Rep 68 when the ITR is in either a linear duplex or hairpin conformation. This binding serves to position Rep 68 or Rep 78 subunit for cleavage at the trs which occurs in a site- and strand-specific manner. The structure of the AAV genome has been well studied, is known to those skilled in the art, and is further discussed in U.S. Pat. Nos. 7,718,424, 8,283,1511, 8,927, 269, and 9,115,373 all of which are incorporated herein by reference.

Previous work has shown that in a permissive cell, heterologous DNA (i.e., non-AAV DNA) flanked by AAV ITRs can be packaged into AAV capsids, providing that the entire DNA construct is less than approximately 5 kb in size. The resulting capsid containing a vector genome is referred to as a recombinant AAV particle. Conventional methods to produce recombinant AAV (rAAV) particles rely on transient co-transfection of mammalian cells with plasmids that provide the AAV structural genes and the ITR-vector genome in trans and the adenovirus helper functions encoding the adenovirus early genes (e.g., E1a, E1b, E4orf6, and VARNA). Expression of the adenovirus proteins render the "permissive" for rAAV production and the resulting AAV gene expression (rep and cap) effectively establishes a "pseudo-infection". Such a cell is capable of ITR-mediated rescue and replication of the AAV vector genome (i.e., any DNA flanked by AAV ITRs), which is provided on a separate plasmid co-transfected into the cell. Expression of the p40 cap gene proteins, VP1, VP2, VP3, and AAP, results in capsid assembly, and the rescued (and replicated) vector genome can then be packaged into the capsids.

While such methods are useful for producing rAAV particles, imprecisions or inefficiencies in the rescue process can cause the rescued ITRs to remain associated with at least a portion of the original plasmid moiety, leading to encapsidation of non-vector DNA (i.e., plasmid "backbone" DNA). Thus, DNA in cis with the ITRs is packaged into AAV particles. Such plasmid DNA (pDNA), which may activate innate immune responses, is considered an impurity since it may be detrimental to therapeutic uses of the recombinant AAV particles. Moreover, plasmid DNA produced in bacterial cells comprises signature DNA methylation patterns, such 5-methyl-adenosine (5mA), and 6-methyl-cytosine (6mC), denoting its origin. Thus, improved methods of providing and delivering AAV vectors are needed. The present disclosure provides such methods, and offers other benefits as well.

SUMMARY

This disclosure provides methods of producing a closed-ended, linear, duplex (CELID) DNA molecule by introducing into a mammalian cell comprising an AAV Rep protein, a nucleic acid molecule comprising heterologous DNA flanked by a pair of inverted terminal repeats (ITRs), each of which forms a T-shaped hairpin structure. At least one inverted terminal repeat (ITR) comprises an AAV Rep protein binding site and an AAV terminal resolution site (trs). The nucleic acid molecule lacks sequences encoding AAV Rep and Cap proteins, and at least one ITR can be used as an origin of replication. The mammalian cell comprising the nucleic acid vector is then cultured under conditions suitable for replication of the nucleic acid molecule. The CELID DNA molecule may then be isolated from the cell.

The mammalian cell used in these methods may be a human cell, such as a HEK-293 cell.

The AAV Rep protein may be produced by vector DNA present in the cell, and the vector DNA may lack an AAV Rep protein binding site, or an AAV trs site, or both. The at least one ITR may be AAV ITR(s).

The heterologous DNA may comprise a sequence encoding a protein, such as an immunogenic protein, a therapeutic protein, and the like. Alternatively, the heterologous DNA may comprise a sequence encoding a therapeutic RNA, such as a siRNA.

This disclosure also provides compositions comprising a CELID DNA molecule produced according to these methods.

Similarly, this disclosure provides methods of producing recombinant AAV (rAAV), by introducing CELID DNA into a cell that contains AAV Rep and Cap proteins, and then culturing the cell comprising the nucleic acid vector under conditions suitable for replication of the nucleic acid vector and expression of the Rep and Cap proteins. rAAV particles may be isolated from the cultured cell.

In these methods, the AAV Rep and Cap proteins may be encoded by vector DNA present in the cell, and the vector DNA may lack one or both of an AAV Rep protein binding site and an AAV trs site. The AAV Rep and Cap proteins may be encoded by nucleic acid molecules inserted into the genome of the cell. These cells may be insect cells, such as Sf9 cells, or mammalian cells, such as HEK-293 cells.

The CELID DNA molecule may comprise heterologous DNA, which may encode a protein, such as an immunogenic protein or a therapeutic protein, or it may encode a therapeutic RNA.

Thus, this disclosure provides rAAV particles produced by these methods and compositions containing the rAAV particles produced by these methods. In these compositions, preferably, the percentage of rAAV particles in the population comprising DNA that is not CELID-derived DNA is less than 50%.

This disclosure provides methods of producing recombinant adeno-associated virus particles (rAAV) in mammalian cells using CELID DNA as the source of the vector genome. Because only AAV vector DNA is in cis with the ITR, encapsidation of non-AAV vector DNA (e.g., plasmid DNA (pDNA)) is effectively prevented. The CELID can be generated in mammalian or invertebrate cell lines, as described in PLoS One. 2013 Aug. 1; 8(8):e69879, and as such reduces or eliminates process impurities of prokaryotic origin (e.g., endotoxin (LPS)) from the final rAAV product. Moreover, CELID DNA produced in such a manner is devoid of signature bacterial DNA methylation, 5-methyl-adenosine (5mA) and 6-methyl-cytosine (6mC). The use of CELID to reduce/eliminate DNA of prokaryotic origin represents a substantial improvement over conventional plasmid transfection methods.

This disclosure also provides therapeutic methods of protecting an individual against a disease, by administering rAAV particles or compositions containing them to an individual in need of such protection. Similarly, these methods may comprise treating an individual for a disease or ameliorating disease in an individual, by administering rAAV particles containing such CELID DNA to an individual suffering from a disease in need of such treatment.

BRIEF DESCRIPTION OF DRAWING

FIG. 1 is a schematic representation of plasmid DNA. An exemplary plasmid ("pFBGR-bsd") contains the green fluorescent protein (GFP) gene under the dual control of the cytomegalovirus IE promoter (CMV) and baculovirus p10 promoter (p10) flanked by AAV-2 inverted terminal repeats (ITR). In the diagram; bla, b-lactamase (ampicillin-resistance gene), bsd, blasticidin-S deaminase gene, ColE1, bacterial origin of replication. (Lower) Linear illustration of pFBGR-bsd indicates the rescued forms of the ITR-flanked transgene. The linear, single-stranded AAV virion genome is represented by a solid thin line flanked by the inverted terminal repeats (ITRs, filled rectangles). The duplex CELID-vector DNA is represented by the open rectangle flanked by four AAV ITRs.

DETAILED DESCRIPTION

The present disclosure provides composition of materials comprised of a recombinant adeno-associated virus capsid and vector genome comprised of DNA of non-bacterial origin. The non-bacterial DNA is CELID which is generated in eukaryotic cells comprised of the heterologous gene and AAV inverted terminal repeats. Also disclosed are novel methods for producing a unique form of an adeno-associated virus (AAV) vector referred to as CELID DNA, improved methods of producing CELID DNA, and methods of using CELID DNA to produce recombinant viral particles for in vitro, ex vivo, or in vivo delivery of exogenous DNA sequences to a cell, tissue, organ, or individual. This disclosure also provides methods of using such recombinant particles to prevent and treat disease. Methods of the disclosure can generally be practiced by introducing into an invertebrate or mammalian cell capable of replicating an AAV genome, a nucleic acid molecule comprising ITRs having AAV-genome replication signals, or CELID DNA, culturing the cell, and isolating newly produced CELID DNA from the cell. Methods of the invention can also be practiced by introducing CELID DNA into an invertebrate or mammalian cell comprising AAV capsid proteins, culturing the cell, and isolating rAAV particles comprising CELID DNA.

This disclosure is not limited to particular embodiments described, as such may vary. The terminology used herein is for the purpose of describing particular embodiments only, and is not intended to be limiting, since the scope of this disclosure will be limited only by the claims.

As used herein and in the appended claims, the singular forms "a," "an," and "the" include plural referents unless the context clearly dictates otherwise. For example, a nucleic acid molecule refers to one or more nucleic acid molecules. As such, the terms "a," "an," "one or more," and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in the recitation of claim elements, or use of a "negative" limitation.

As used herein, the terms "nucleic acid molecule," and "polynucleotide," refer to a DNA or RNA molecule, or a hybrid thereof. Such nucleic acid molecules can also be modified to alter certain characteristics; for example, resistance to degradation. A modified nucleic acid molecule is one comprising one or more nucleotides that are similar to the parent nucleotides, but which contain chemical modifications that alter the properties of the nucleic acid molecule. Examples of modified nucleic acid molecules are disclosed in U.S. Pat. Nos. 8,765,703 and 8,946,183, which are incorporated herein by reference.

As used herein, CELID DNA refers to a linear, duplex DNA molecule comprising heterologous DNA flanked by inverted terminal repeats (ITRs), at least one of which comprises an AAV Rep protein binding site and an AAV trs site, wherein the linear, duplex DNA molecule has covalently closed ends. Because the ends are covalently closed, CELID DNA is exonuclease resistant.

As used herein, the phrase "heterologous DNA sequence" refers to DNA from a species other than adeno-associated virus (AAV). Thus, heterologous DNA is not normally found in, or associated with, AAV DNA. For example, a DNA sequence encoding a human protein, a bacterial protein, or a protein from a virus other than AAV, would be considered a heterologous DNA sequence.

As used herein, the phrase "flanked by inverted terminal repeats" means the heterologous DNA is located between at least two inverted terminal repeats. That is, the 5' end of the heterologous DNA is joined to an ITR and the 3' end of the heterologous DNA is joined to an ITR. The heterologous DNA may be joined directly to the ITRs (i.e., no intervening nucleotide sequence), or it may be separated from the ITR sequences by other nucleotide sequences. In certain embodiments, each single, linear strand of heterologous DNA in the duplex molecule is between two, full-length AAV ITRs. Because each linear strand of a CELID DNA molecule pairs with a complementary strand, in certain embodiments the final, duplex CELID molecule comprises a total of four ITRs. The general structure of CELID DNA is disclosed in Li et al., PLoS One, 2013, supra, and is also illustrated in FIG. 1.

As used herein, an inverted repeat (IR) refers to a first sequence of nucleotides followed at its 3' end by a second sequence of nucleotides that is the reverse complement of the first sequence of nucleotides. Such sequences are known to those skilled in the art. The inverted repeat can comprise an intervening sequence of nucleotides between the first sequence and its reverse complement, and the length of the intervening sequence be any length including zero. For example, the sequence ACTG-CAGT is an inverted repeat sequence having no intervening nucleotides. An inverted terminal repeat (ITR) refers to an inverted repeat located at the end (the termini) of a linear DNA molecule. Preferred ITRs to use in methods of the present disclosure are ITRs from the AAV genome. The existence of ITRs at the end of AAV genomes is well known to those skilled in the art.

This disclosure provides methods of producing a closed-ended, linear, duplex (CELID) DNA molecule comprising:

a) introducing into an invertebrate or mammalian cell comprising one or more polynucleotide sequence encoding one or more AAV Rep proteins, a nucleic acid molecule comprising heterologous DNA flanked by a pair of inverted terminal repeats (ITRs);
wherein at least one inverted terminal repeat (ITR) comprises an AAV Rep protein binding site and an AAV terminal resolution site (trs); and,
wherein at least one ITR can be used as an origin of replication;

b) culturing the mammalian cell under conditions suitable for replication of the nucleic acid molecule, thereby producing new CELID DNA molecules; and, c) isolating the newly produced CELID DNA molecules from the cell.

In one embodiment, the nucleic acid molecule is a plasmid. In one embodiment, the nucleic acid molecule is CELID DNA.

Methods of this disclosure utilize nucleic acid sequences, polynucleotide sequences, and proteins from adeno-associated virus (AAV). Such nucleic acid sequences, polynucleotides, and proteins can be from any serotype of AAV. Examples of such serotypes include, but are not limited to, AAV1, AA2, AAV3, AAV4, AAV5, AAV6, AAV7, AAV8, AAV9, AAV10, AAV11, AAV12, avian adeno-associated virus (AAAV), bovine adeno-associated virus (BAAV), AAV rh10 and Anc80. Additional serotypes useful for practicing the methods of this disclosure are described in U.S. Pat. No. 8,283,1511, which is incorporated herein in its entirety. Moreover, it will be appreciated by those skilled in the art that nucleic acid sequences, polynucleotides and proteins from several different AAV serotypes can be used in the same method. For example, the Rep protein may be from AAV5, whereas the Rep-binding site present in the ITRs may be from AAV2.

Any invertebrate or mammalian cell capable of being transfected and supporting replication of an AAV genome can be used to practice aspects of the present disclosure. Examples of suitable mammalian cells include, but are not limited to, human embryonic kidney cells 293 (also referred to herein as HEK 293, or HEK-293 cells), HeLa cells, NIH3T3 cells, Huh-7 cells, 911 cells, Hep1A cells, HepG2 cells, CHO cells, MeWo cells, COS cells, HT1180, A549 cells, monocytes, and dendritic cells. Methods of this disclosure may also be practiced using invertebrate cells, such as insect cells, one example of which are *Spodoptera frugiperda* cells (e.g., SF9 cells).

Invertebrate and mammalian cells used in methods of this disclosure may comprise one or more polynucleotide sequences encoding one or more AAV Rep proteins. In one aspect, the one or more polynucleotide sequences encode at least one AAV Rep protein selected from the group consisting of a AAV Rep78 protein, a AAV Rep68 protein, a AAV Rep52 protein and a AAV Rep 40 protein. In one aspect, the one or more polynucleotide sequences encode a AAV Rep 78 protein and at least one AAV Rep protein selected from the group consisting of a AAV Rep68 protein, a AAV Rep52 protein and a AAV Rep 40 protein. In one aspect, the cell comprises one or more polynucleotides sequences encoding an AAV Rep 78 protein and a AAV Rep68 protein. In one aspect, the cell comprises one or more polynucleotide sequences encoding an AAV Rep78 protein and a AAV Rep52 protein. In one aspect, the one or more polynucleotide sequences encode at least one AAV Rep protein comprising a sequence at least 90%, at least 95% or at least 100% identical to the full-length of a AAV protein from a AAV virus selected from the group consisting of AAV1, AA2, AAV3, AAV4, AAV5, AAV6, AAV7, AAV8, AAV9, AAV10, AAV11, AAV12, AAAV, BAAV, AAV rh10 and Anc80, and a serotype disclosed in U.S. Pat. No. 8,283,151.

Polynucleotide molecules encoding one or more AAV Rep proteins may comprise one or more control elements operably linked to nucleotide sequences encoding the AAV Rep proteins. As used herein, a control element is a DNA sequence that is physically linked with nucleotide sequence encoding a protein (e.g., AAV Rep protein), or a therapeutic RNA, and which directs or regulates transcription of the corresponding RNA when introduced into a cell. Examples of control elements include, but are not limited to, promoter sequences, enhancer sequences, repressor sequences and the like.

Cells comprising one or more polynucleotide sequences encoding one or more AAV Rep proteins can be produced using methods known to those skilled in the art. For example, nucleic acid molecules encoding an AAV Rep protein can be introduced into cells by transient transfection techniques (e.g., liposomal, calcium phosphate precipitation, polyethylenimine transformation, etc.) or by physical means (e.g., electroporation, microinjection) known to those skilled in the art. Such molecules can be linear (e.g., PCR product), or they can be a nucleic acid vector. Examples of such vectors include, but are not limited to, plasmids, cosmids, and viral vectors. As used herein, a viral vector refers to a nucleic acid molecule constructed from viral genomic DNA, and which comprises a gene of interest (e.g. a nucleic acid molecule encoding a AAV Rep protein) to be carried into a cell. Such viral vectors can, but need not, lack sequences encoding proteins necessary for viral replication in invertebrate or mammalian cells (e.g., viral polymerase, viral capsid proteins, etc.). Such vectors may also lack viral sequences necessary for replication of the vector (e.g., replicase protein binding sites, promoters, etc.) in vertebrate or mammalian cells. Such vectors are known to those skilled in the art and include, but are not limited to, adenovirus vectors, AAV vectors, baculovirus vectors, lentivirus vectors, herpesvirus vectors and retrovirus vectors. In viral vectors, such nucleic acid molecules can also be packaged using viral proteins to form virus particles, virus-like particles (VLPs) or pseudovirus particles, and the viral vector delivered into the cell by viral transfection (also referred to as viral transinfection) of the cell. A cell comprising one or more polynucleotide sequences encoding an AAV Rep protein may be produced by introducing into the cell one or more linear polynucleotide molecules encoding an AAV Rep protein, or one or more nucleic acid vector(s) encoding an AAV Rep protein, or one or more plasmids encoding the AAV Rep protein, or one or more cosmids encoding an AAV Rep protein, or one or more viral vectors encoding an AAV Rep protein, or by transfecting the cell with one or more viruses, VLPs, or pseudovirus vectors encoding an AAV Rep protein.

It will be understood by those skilled in the art that nucleic acid molecules comprising polynucleotide sequences encoding an AAV Rep protein will comprise a polynucleotide sequence encoding the AAV Rep protein operably linked to one more control elements. As used herein, a control element is a DNA sequence that is physically linked with a DNA sequence, and that directs or regulates expression from the linked DNA sequence when introduced into a cell. For example, a control element linked to a DNA sequence encoding an AAV Rep protein will regulate or direct expression of the encoded AAV Rep protein. Examples of control elements include, but are not limited to, promoter sequences, enhancer sequences, repressor site sequences, and the like. Typically, control elements used to direct or regulate expression from DNA are selected to function in the cell into which the nucleic acid molecule is introduced. For example, preferred control elements for practicing the instant invention are control elements that function in mammalian and invertebrate cells. In certain aspects, control elements can be from AAVs. Appropriate control elements can be selected by those skilled in the art.

CELID DNA may be purified from the cells used in these methods. To minimize contamination of the purified CELID DNA, steps should be taken to recover highly purified, homogenous CELID from the cells, thereby avoiding carryover of baculovirus DNA, cellular DNA, and AAV rep DNA. For example, one way to do this is to reduce or eliminate the ability of the AAV Rep-encoding polynucleotide molecule to replicate in invertebrate and/or mammalian cells. Thus, in one aspect, the one or more polynucleotide molecules encoding one or more AAV Rep proteins are unable to replicate in the invertebrate or mammalian cell.

A cell comprising one or more polynucleotide sequences encoding one or more AAV Rep proteins can be a cell in which one or more polynucleotide molecules are stably inserted into the genome of the cell. Such cells are usually created by introducing into the cell one or more one or more polynucleotide molecules comprising a gene of interest (e.g., a AAV rep gene) and a selectable marker, and allowing the cell to undergo several generations of cell division while also selecting for cells that stably express the selectable marker. Methods of making such cells are known to those skilled in the art. Thus, in one aspect, the genome of the invertebrate of mammalian cell comprises one or more polynucleotide sequence(s) encoding one or more AAV Rep proteins.

In certain aspects of the invention, the nucleic acid molecule (e.g., CELID DNA) introduced into the invertebrate or mammalian cell comprises a binding sequence at which an AAV Rep protein can act (i.e., a Rep binding site). Thus, in certain aspects, the nucleic acid molecule introduced into the cell comprises an AAV Rep protein binding site. Examples of suitable Rep protein binding sites include, but are not limited to, polynucleotide sequences comprising GCTC or multiples thereof (e.g., (GCTC)×3, (GCTC)×4). In one aspect, the Rep protein binding site is from an AAV virus selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 6,984,517 (to Chiorini et al. issued January 2006); U.S. Pat. No. 7,718,424 (to Chiorini et al. issued May 2010); U.S. Pat. No. 8,927,269 (to Bossis et al. issued January 2015); and, U.S. Pat. No. 8,283,1511 (to Schmidt et al. issued October 2012) the disclosures of which are each incorporated herein in their entirety. Similarly, sequences suitable for such sites are known to those skilled in the art, and are also disclosed in the U.S. Patents listed above and incorporated herein.

In certain aspects of the invention, the nucleic acid molecule introduced into the invertebrate or mammalian cell (e.g., CELID DNA) comprises an AAV terminal resolution site (trs). One example of a suitable trs is a sequence comprising RGTTGR, where R is a purine. In one aspect, the trs is from an AAV virus selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151. Sequences suitable for such sites are known to those skilled in the art, and are also disclosed in U.S. Pat. No. 8,283,151.

As specified in the afore-mentioned method, the nucleic acid molecule comprising heterologous DNA introduced into the invertebrate or mammalian cell (e.g., CELID DNA), comprises ITRs. Such ITRs allow recognition by AAV proteins, thereby facilitating replication of the nucleic acid molecule. It is well known in the field of AAV biology that adeno-associated viruses comprise ITRs at the ends of their genomes. Thus, the ITRs flanking the heterologous DNA may comprise sequences at least 90%, or at least 95% identical to the full-length sequence of AAV ITRs, wherein at least one ITR in the nucleic acid molecule comprises one or both of an AAV Rep protein binding site, and an AAV trs. In certain aspects, the ITRs flanking the heterologous DNA may comprise sequences identical to the full-length sequence of AAV ITRs. The ITRs flanking the heterologous DNA may comprise sequences at least 90%, or at least 95%, or 100% identical to the full-length polynucleotide sequence of the ITRs from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151, wherein at least one ITR comprises an AAV Rep protein binding site, and/or an AAV trs site. As described above, the AAV elements (i.e., Rep binding site, trs, ITR) may be from the same, or different, serotype of AAV. For example, the ITR sequences may be at least 90%, or at least 95%, or 100% identical to the ITR sequences of AAV2, while the Rep binding site may be from AAV5 and the trs from AAV5, or alternatively, another AAV, such as AAV4.

Once the nucleic acid molecule comprising the heterologous DNA flanked by ITRs (e.g., CELID DNA) has been introduced into the invertebrate or mammalian cell, the cells are cultured under conditions suitable for replication of the nucleic acid molecules. Such conditions are known to those skilled in the art, and are also described in U.S. Patent Publication No. 2014/0107186, which is incorporated by reference in its entirety. Preferred cell culture conditions are those that induce Rep protein expression within the mammalian cell, rescue of the heterologous DNA and flanking ITRs from the nucleic acid molecule, and that result in the production of new CELID DNA.

Following culture of the cells for an appropriate length of time, DNA is purified from the cells to obtain isolated (purified) CELID DNA. As used herein, the terms "isolated" and "purified" do not refer to a specific, numerical level of purity of a solution comprising CELID DNA. Instead, such terms refer to the fact that the CELID DNA has been separated from at least some components of the cell culture environment. For example, isolated and purified can refer to CELID DNA present in a cell that has been removed from a culture dish, homogenized, and subjected to low speed (e.g., 500×G) centrifugation. Alternatively, isolated and purified can refer to CELID DNA purified using, for example, column chromatography or gradient centrifugation. Methods of purifying the CELID DNA are known to those skilled in the art. Examples of such methods include, but are not limited to, precipitation and chemical isolation, chromatography (e.g., Sartobind Q), nucleic acid-binding beads, and commercial kits (e.g., QIAGEN™ DNA purification kits, PROMEGA™ PUREYIELD™ DNA purification kits, etc.). Alternatively, CELID DNA can be purified in the form of exosomes or microparticles. Examples of suitable methods are disclosed in U.S. Patent Publication No. 2014/0107186 and in Li et al.

Heterologous DNA present in CELID DNA of this disclosure may encode a therapeutic molecule. As used herein, a "therapeutic molecule" is a molecule that, when administered (either directly or by intracellular expression from CELID DNA) to a person having a disease or illness, results in a clinically significant improvement in one or more symptoms of the disease or illness. Thus, the CELID DNA may encode a therapeutic protein. Examples of therapeutic proteins include, enzymes, receptors, ligands, and the like. The therapeutic molecule may be a therapeutic nucleic acid molecule. Therapeutic nucleic acid molecules may be one or more of a siRNA, a RNAi, a shRNA, a miRNA, an aptamer, and a ribozyme. Examples of such therapeutic RNAs are disclosed in U.S. Pat. No. 8,987,225 (to Collard et al, issued March 2015), which is incorporated herein by reference.

Heterologous DNA present in CELID DNA of this disclosure may also encode an immunogenic protein. As used herein, an immunogenic protein is a protein which, when administered to an individual, results in the development in the individual of a humoral and/or a cellular immune response to the protein or a bacteria or virus comprising the protein. As used herein, a "humoral immune response" refers to an immune response mediated by antibody molecules, including secretory IgA, or IgG molecules, while a "cellular immune response" is one mediated by T-lymphocytes and/or other white blood cells. A cellular immune response may also refer to the production of cytokines, chemokines and other such molecules produced by activated T-cells and/or other white blood cells, including those derived from CD4+ and CD8+T-cells.

Immunogenic proteins may be from any organism in which it is desirable to elicit an immune response. The heterologous DNA may encode a bacterial protein or a viral protein.

To express the therapeutic nucleic acid molecules, therapeutic proteins, and immunogenic proteins encoded within the heterologous DNA, the heterologous DNA may be operably linked to one or more control elements.

One aspect of the invention is a method of producing a CELID DNA molecule comprising:
  a) introducing into an invertebrate or mammalian cell, a nucleic acid molecule comprising heterologous DNA flanked by a pair of inverted terminal repeats (ITRs);
      wherein at least one inverted terminal repeat (ITR) comprises an AAV Rep protein binding site and an AAV terminal resolution site (trs);
      wherein at least one ITR can be used as an origin of replication; and
      wherein the nucleic acid molecule lacks sequences encoding AAV Rep and Cap proteins;
  b) introducing into the mammalian cell, one or more polynucleotide molecules encoding one or more AAV Rep protein;
  c) culturing the mammalian cell under conditions suitable for producing CELID DNA; and, d) isolating the newly produced CELID DNA from the cultured cell.

In one aspect, the nucleic acid molecule introduced into the cell is CELID DNA. Thus, one aspect of the invention is a method of producing CELID DNA comprising:
a) introducing into an invertebrate or mammalian cell, CELID DNA comprising heterologous DNA flanked by a pair of inverted terminal repeats (ITRs);
   wherein at least one inverted terminal repeat (ITR) comprises an AAV Rep protein binding site and an AAV terminal resolution site (trs);
   wherein at least one ITR can be used as an origin of replication; and
   wherein the CELID DNA lacks sequences encoding AAV Rep and Cap proteins;
b) introducing into the mammalian cell, one or more nucleic acid molecules encoding one or more AAV Rep protein;
c) culturing the mammalian cell under conditions suitable for replication of the CELID DNA; and,
d) isolating the newly replicated CELID DNA molecule from the cultured cell.

In the methods disclosed above, steps (a) and (b) can be performed in any order, or at the same time. For example, the one or more polynucleotide molecules encoding one or more AAV Rep proteins may be introduced in the mammalian cell first, after which the nucleic acid molecule, or CELID DNA, can be introduced into the mammalian cell. The important aspect is that the nucleic acid molecule, or CELID DNA, and the AAV Rep protein interact within the cell. Thus, in one aspect, the AAV Rep protein-encoding polynucleotide molecule and the nucleic acid molecule, or CELID DNA, may be introduced into the cell at the same time.

In one aspect, the ITRs flanking the heterologous DNA comprise sequences at least 90%, or at least 95% or 100% identical to the full-length polynucleotide sequence of AAV ITRs, wherein at least one ITR comprises an AAV Rep protein binding site, and/or an AAV trs site. The ITRs flanking the heterologous DNA may comprise sequences at least 90%, or at least 95%, or 100% identical to the full-length polynucleotide sequence of the ITRs from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151, wherein at least one ITR comprises an AAV Rep protein binding site, and/or a AAV trs site, and the ITRs may comprise sequences from different serotypes of AAV.

The one or more polynucleotide molecules may encode one or more AAV Rep proteins selected from the group consisting of an AAV Rep78 protein, an AAV Rep68 protein, an AAV Rep52 protein, and an AAV Rep 40 protein. For example, the one or more polynucleotide molecules may encode an AAV Rep 78 protein, and at least one AAV Rep protein selected from an AAV Rep68 protein, an AAV Rep52 protein, and an AAV Rep 40 protein. In another example, the one or more polynucleotide molecules may encode an AAV Rep 78 protein and an AAV Rep68 protein. In another example, the one or more polynucleotide molecules may encode an AAV Rep78 protein and a AAV Rep52 protein. In another example, the one or more polynucleotide molecules encode AAV Rep protein from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151.

The one or more polynucleotide molecules encoding one or more AAV Rep proteins may comprise linear nucleic acid molecules, or nucleic acid vectors, or plasmid DNA, or cosmid DNA, or a viral vector. The one or more polynucleotide molecules encoding one or more AAV Rep protein may be introduced into the cell by transfecting the cell with virus particles, VLPs, or pseudoviruses comprising the one or more polynucleotide molecules.

In one aspect, the one or more polynucleotide molecules are unable to replicate in invertebrate or mammalian cells. In one aspect, he one or more polynucleotide molecules encoding may lack one or both of a Rep protein binding site and a trs.

The nucleic acid molecule, or CELID DNA, introduced into the cell may comprise an AAV Rep protein binding site. The AAV Rep protein binding site may comprise GCTC or multiples thereof (e.g., $(GCTC)_3$, $(GCTC)_4$). The Rep protein binding site and the trs may individually be from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151.

Packaging of AAV genomic DNA by AAV capsid proteins is mediated by interactions between AAV capsid proteins, and sequences present in the ITRs of the AAV genome. Thus, because CELID DNA comprises ITRs, CELID DNA can be packaged by AAV capsid proteins, resulting in AAV particles comprising CELID DNA. In accordance with the present disclosure, such AVV particles are referred to as rAAV particles ("rAAV"). Such particles are able to bind to and enter cells. However, because such particles lack nucleic acid sequences encoding AAV Rep and Cap proteins, they are unable to produce progeny virus particles, and are thus ideal vehicles for delivering heterologous DNA into cells in culture or in an individual.

One aspect of the invention is a method to produce rAAV particles comprising heterologous DNA, the method comprising culturing a cell comprising i) CELID DNA comprising heterologous DNA; and, ii) a nucleic acid molecule encoding one or more AAV capsid proteins; and incubating the cell under conditions suitable for the formation or rAAV particles containing the CELID DNA. In one aspect, the rAAV particles can be purified from the cell. Methods of purifying such rAAV particles are known to those skilled in the art.

In one aspect, a method to produce rAAV particles comprising heterologous DNA, comprises:
a) producing or obtaining a cell comprising CELID DNA, wherein the CELID DNA comprises heterologous DNA;
b) introducing into the cell one or more nucleic acid molecules encoding one or more AAV Cap proteins; and
c) incubating the cell under conditions suitable for the formation of rAAV particles comprising the CELID DNA.

In one aspect, a method to produce rAAV particles comprising heterologous DNA, comprises:
a) producing or obtaining a cell comprising one or more nucleic acid molecules encoding one or more AAV capsid proteins;
b) introducing CELID DNA into the cell, wherein the CELID DNA comprises heterologous DNA; and
d) incubating the cell under conditions suitable for the formation of rAAV particles comprising the CELID DNA.

A related method of this disclosure for producing rAAV particles comprising heterologous DNA, comprises:
a) introducing CELID DNA into a cell comprising one or more nucleic acid molecules encoding one or more AAV capsid proteins, wherein the one or more nucleic acid molecules are stably inserted into the genome of the cell; and,
e) incubating the cell under conditions suitable for the formation of rAAV particles comprising the CELID DNA.

In certain aspects of the afore-mentioned methods, the cell further comprises a nucleic acid molecule encoding an AAV Rep protein. Thus, one aspect of the invention is a method to produce rAAV particles comprising heterologous DNA, the method comprising:
a) culturing a cell comprising:
i) CELID DNA comprising heterologous DNA;
ii) one or more nucleic acid molecules encoding one or more AAV Cap proteins; and,
iii) one or more polynucleotide molecules encoding one or more AAV Rep proteins;
under conditions suitable for replication of the CELID DNA, and expression of the encoded Rep and Cap proteins; and,
b) isolating rAAV particles from the cultured cell.

It will be understood by those skilled in the art that in such a method, an AAV Cap protein and an AAV Rep protein can be encoded by the same nucleic acid molecule or polynucleotide molecules, or they can be encoded by different nucleic acid or polynucleotide molecules. Thus, in one aspect, at least one of the one or more nucleic acid or polynucleotide molecules encodes an AAV Cap protein and an AAV Rep protein. In one aspect, the one or more AAV Cap proteins are encoded by one or more nucleic acid molecules that do not encode an AAV Rep protein. In one aspect, the one or more AAV Rep proteins are encoded by one or more polynucleotide molecules that do not encode an AAV Cap protein.

In certain aspects, the one or more nucleic acid molecules are unable to replicate in the cultured cell. In certain aspects, the one or more polynucleotide molecules are unable to replicate in the cultured cell. In certain aspects, the one or more nucleic acid molecules, and/or the one or more polynucleotide molecules, are present in one or more vectors such as, for example, a plasmid vector. In certain aspects, the one or more vectors lack the ability to replicate in the cultured cell. In certain aspects, the one or more nucleic acid molecules, and/or the one or more polynucleotide molecules, are present in the genome of the cell.

One aspect of the invention is a method to produce rAAV particles comprising heterologous DNA, comprises:
a) producing or obtaining a cell comprising CELID DNA, wherein the CELID DNA comprises heterologous DNA;
b) introducing into the cell one or more nucleic acid molecules encoding one or more AAV Cap proteins, and one or more polynucleotide molecules encoding one or more AAV Rep proteins; and
c) incubating the cell under conditions suitable for the formation of rAAV particles comprising the CELID DNA.

In one aspect, a method to produce rAAV particles comprising heterologous DNA, comprises:
a) producing or obtaining a cell comprising one or more nucleic acid molecules encoding one or more AAV capsid proteins, and one or more polynucleotide molecules encoding one or more AAV Rep proteins;
b) introducing into the cell CELID DNA, wherein the CELID DNA comprises heterologous DNA; and
c) incubating the cell under conditions suitable for the formation of rAAV particles comprising the CELID DNA.

A related method of this disclosure, for producing rAAV particles comprising heterologous DNA, comprises:
a) producing or obtaining a cell comprising: i) one or more nucleic acid molecules encoding one or more AAV capsid proteins; and ii) one or more polynucleotide molecules encoding one or more AAV Rep proteins, wherein the one or more nucleic acid molecules and/or the one or more polynucleotide molecules are stably inserted into the genome of the cell;
b) introducing CELID DNA into the cell, wherein the CELID DNA comprises heterologous DNA; and,
c) incubating the cell under conditions suitable for the formation of rAAV particles comprising the CELID DNA.

In the aforementioned methods, any cell can be used to produce rAAV comprising the CELID DNA comprising heterologous DNA, so long as the cell allows the assembly of rAAV particles comprising CELID DNA. The cell may be an invertebrate cell, such as an insect cell, one example of which is an Sf9 cell. The cell may be a mammalian cell, including a cell selected from the group consisting of human embryonic kidney 293 cells, HeLa cells, NIH3T3 cells, Huh-7 cells, 911 cells, Hep1A cells, HepG2 cells, CHO cells, MeWo cells, COS cells, HT1180, A549 cells, monocytes, and dendritic cells.

In the aforementioned methods, the CELID DNA introduced in the cell can be produced using any cell capable of producing CELID DNA comprising heterologous DNA. Preferred cells are those in which the CELID DNA produced lacks bacterial methylation patterns. In some aspects, the cell used to produce CELID DNA are invertebrate cells or mammalian cells. Methods of producing CELID DNA comprising heterologous DNA, and that is suitable for use in the disclosed methods, are disclosed herein, and are also disclosed in the art. (e.g., Li et al. PLoS One. 2013, supra).

Methods of producing a cell comprising CELID DNA, nucleic acid molecules encoding AAV Cap proteins, or polynucleotides encoding AAV Rep proteins, are known to those skilled in the art. For example, CELID DNA, nucleic acid molecules encoding AAV Cap proteins, or polynucleotides encoding AAV Rep proteins, can be introduced into cells by transient transfection techniques (e.g., liposomal, calcium phosphate precipitation, etc.) or by physical means (e.g., electroporation, microinjection, etc.) known to those skilled in the art. Nucleic acid molecules and polynucleotide molecules can be introduced as linear molecules (e.g., PCR product) or in a nucleic acid vector. Examples of such vectors include, but are not limited to, plasmids, cosmids, and viral vectors.

In the aforementioned methods, CELID DNA introduced into the cell comprises heterologous DNA flanked by two AAV ITRs. In certain aspects, the ITRs flanking the heterologous DNA may comprise sequences at least 90%, or at least 95%, or 100% identical to the full-length polynucleotide sequence of AAV ITRs, wherein at least one ITR comprises an AAV Rep protein binding site, and/or an AAV trs site. The ITRs flanking the heterologous DNA may comprise sequences at least 90%, or at least 95%, or 100% identical to the full-length polynucleotide sequence of the ITRs from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151, wherein at least one ITR comprises an AAV Rep protein binding site, and/or a AAV trs site. The ITRs may comprise sequences from the same serotype of AAV or from different serotypes of AAV.

In the aforementioned methods, the CELID DNA introduced into the cell may comprise an AAV Rep protein binding site, such as a AAV Rep protein binding site comprising GCTC or multiples thereof (e.g., $(GCTC)_3$, $(GCTC)_4$). The Rep protein binding site may be from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151. The CELID DNA may also comprise an AAV trs from an AAV virus selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151.

In the aforementioned methods, CELID DNA may comprise heterologous DNA encoding a therapeutic molecule, such as a therapeutic protein (such as an enzyme, a receptor, a ligand and a hormone), or a therapeutic nucleic acid molecule. Examples of therapeutic proteins include, enzymes, receptors, ligands, and the like. Therapeutic nucleic acid molecules may be one or more of a siRNA, a RNAi, a shRNA, a miRNA, an aptamer, and a ribozyme.

The CELID DNA may comprise heterologous DNA encoding an immunogenic protein. Immunogenic proteins may be from any organism in which it is desirable to elicit an immune response. The heterologous DNA may encode a bacterial protein or a viral protein.

To express the therapeutic nucleic acid molecules, therapeutic proteins, and immunogenic proteins encoded within the heterologous DNA, the heterologous DNA may be operably linked to one or more control elements, such as a promoter sequence or regulatory sequence.

The use of AAV capsid proteins to produce AAV particles comprising nucleic acid molecules other than the AAV genome is known in the art and is also discussed in U.S. Patent Publication Nos. 2003/0148506 and 2004/0197895, both of which are incorporated herein by reference. AAV capsid proteins include viral protein-1 (VP1), virus protein-2 (VP2) and virus protein-3 (VP3). Thus, nucleic acid molecules used in the disclosed methods may encode VP1, VP2, VP3, or combinations thereof, including each of VP1, VP2, and VP3. During a natural infection of a cell with AAV, all three proteins are encoded by a single transcript, and the different proteins produced by alternative splicing and utilization of alternative start sites. Thus, all three capsid proteins may be encoded on a single nucleic acid molecule. Alternatively, each capsid protein may be encoded by a separate nucleic acid molecule. In such an embodiment, each nucleic acid molecule would need to be introduced into the cell. In certain aspects, one or more nucleic acid sequences encoding one or more capsid proteins selected from the group consisting of VP1, VP2 and VP3, may be stably inserted into the genome of the cell.

The AAV capsid proteins used in making rAAVs of this disclosure can come from any serotype of AAV, so long as such proteins are capable of forming rAAV particles. Thus, capsid proteins used to produce rAAVs of this disclosure may be from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151. The AAV capsid protein may comprise an amino acid sequence at least 80%, at least 85%, at least 90%, at least 95%, at least 97%, or 100% identical to the amino acid sequence of a capsid protein from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151.

As has been discussed, AAV capsid proteins package the AAV genomic DNA into virus particles utilizing sequences present in the ITRs of the genome. However, the packaging of DNA by capsid proteins is somewhat flexible with regard to the origin of the ITRs sequences. For example, it has been demonstrated that DNA having AAV2 ITRs can be packaged into VLPs using capsid proteins from AAV1, AAV2, AAV3, AAV4 and AAV5 (Rabinowitz J E, Rolling F, Li C, Conrath H, Xiao W, Xiao X, Samulski R J. *Cross-packaging of a single adeno-associated virus (AAV) type 2 vector genome into multiple AAV serotypes enables transduction with broad specificity*. J Virol. 2002 January; 76(2):791-801). Thus, the capsid proteins used to produce rAAVs of this disclosure may, but need not, be from the same serotype of virus as the ITRs present in the CELID DNA, or DNA comprising ITRs and heterogeneous DNA used to produce CELID DNA.

In certain aspects, the one or more nucleic acid molecules encoding one or more AAV Cap proteins is/are unable to replicate in the cell. In certain aspects, the one or more nucleic acid molecules encoding one or more AAV Cap proteins, may lack an AAV Rep protein binding site. In certain aspects, the one or more nucleic acid molecules encoding an AAV Cap protein may comprise one more control elements operably linked to the AAV Cap-encoding nucleotide sequences in the nucleic acid, or polynucleotide, molecules.

In the aforementioned methods, polynucleotide molecules encoding the one or more AAV Rep proteins may encode an AAV Rep protein selected from the group consisting of a AAV Rep78 protein, a AAV Rep68 protein, a AAV Rep52 protein, an AAV Rep 40 protein, and combinations of these AAV Rep proteins. The AAV Rep protein may be from an AAV selected from the group consisting of AAV1, AA2, AAV3, AAV4, AAV5, AAV6, AAV7, AAV8, AAV9, AAV10, AAV11, AAV12, AAAV, BAAV, and a serotype disclosed in U.S. Pat. No. 8,283,151. A cell comprising one or more polynucleotide molecules encoding one or more AAV Rep proteins may be produced by introducing into a cell any one or more of the polynucleotide molecules described herein. In certain aspects, the one or more polynucleotide molecules encoding one or more AAV Rep proteins are unable to replicate in invertebrate or mammalian cells.

As an alternative to introducing a nucleic acid molecule encoding a AAV Cap protein into a cell, cells can be produced in which one or more nucleotide molecules encoding one or more AAV Cap proteins is stably inserted into the genome of the cell. Likewise, cells used in methods of the present disclosure may comprise AAV-Rep-encoding polynucleotide molecules stably inserted into the genome of the cell. Such cells are usually created by introducing into the cell a nucleic acid molecule comprising a gene of interest (e.g., the AAV Cap gene) and a selectable marker, and allowing the cell to undergo several generations of replication while also selecting for cells that stably express the selectable marker. Methods of making such cells are known to those skilled in the art. Thus, the genome of the cells used in the methods of this disclosure may comprise one or more nucleic acid molecules encoding a AAV Cap protein, and/or one or more polynucleotide molecules encoding an AAV Rep protein.

As previously discussed, current methods for producing rAAV particles yield particles in which the rescued ITRs to remain associated with at least a portion of the original plasmid moiety from which they were obtained, leading to encapsidation of non-vector DNA (i.e., plasmid DNA). Thus, rAAV particles produced using current methods contain nucleic acid impurities, which may activate innate immune responses, thereby impairing therapeutic uses of the particles. Because methods of the instant invention use CELID DNA, which lacks such contaminating nucleic acid sequences, the present invention provides rAAV particles that are safer than particles produced by previously available methods Thus, one aspect of the invention is an rAAV particle, wherein the rAAV comprises CELID-derived DNA comprising heterologous DNA, and wherein contaminating DNA makes up less than 10% of the total amount of DNA in the particle. As used herein, the term contaminating DNA refers to DNA from a source other than adenoassociated virus, and excludes the heterologous DNA in the CELID DNA. For example, if the rAAv particle contained CELID DNA comprising a gene encoding an influenza virus hemagglutinin (HA) protein, contaminating DNA would be any DNA other than AAV DNA and DNA encoding an influenza hemagglutinin protein. Examples of contaminating DNA include, but are not limited to, plasmid DNA, bacterial DNA, and DNA from a mammalian cell genome (other than genomic DNA used as heterologous DNA). rAAV particles in which contaminating DNA makes up less than 10% of the total amount of DNA in the particle are made using the methods disclosed herein. In certain aspects, the heterologous DNA encodes an immunogenic protein, a therapeutic protein, or a therapeutic RNA. In certain aspects, contaminating DNA makes up less than 1% of the total amount of DNA in the particle. In certain aspects, contaminating DNA makes up less than 0.1% of the total amount of DNA in the particle. In certain aspects, contaminating DNA makes up less than 0.01% of the total amount of DNA in the particle. In certain aspects, the rAAV particle lacks contaminating DNA.

This disclosure also provides methods for treating an individual for an illness comprising administering to the individual a rAAV particle of the invention, wherein the rAAV comprises CELID DNA comprising heterologous DNA encoding a therapeutic molecule suitable for treatment of the illness. The terms individual, subject, and patient are well-recognized in the art, and are herein used interchangeably to refer to any human or other animal capable of being virally transfected by a rAAV of this disclosure.

This disclosure also provides methods for eliciting an immune response (e.g. vaccinating) in an individual, comprising administering to the individual a rAAV particle of the invention, wherein the rAAV comprises CELID DNA comprising heterologous DNA encoding an immunogenic polypeptide. The immunogenic polypeptide may be from a bacteria or a virus. The immunogenic polypeptide may be from a virus selected from the group consisting of adenoviruses, herpesviruses, papilloma viruses, polyomaviruses, hepadnaviruses, parvoviruses, astroviruses, calciviruses, picornaviruses, coronaviruses, flaviviruses, togaviruses, hepeviruses, retroviruses, orthomyxoviruses, arenaviruses, bunyaviruses, filoviruses, paramyxoviruses, rhabdoviruses, reoviruses, and poxviruses.

This disclosure also includes kits suitable for producing CELID DNA, and/or rAAV particles of the disclosure. Kits may include, for example, recombinant virus vectors of this disclosure, nucleic acid molecules for constructing CELID DNA and/or rAAV particles of this disclosure, and/or complementing cells for producing rAAV particles of this disclosure. Kits may also comprise associated components, such as proteins, enzymes, cell culture media, buffers, labels, containers, vials, syringes, instructions for using the kit, and the like.

The foregoing description has been presented for purposes of illustration and description. The description is not intended to limit the invention to the form disclosed herein. Consequently, variations and modifications commensurate with the above teachings, and the skill or knowledge of the relevant art, are within the scope of the present invention. The embodiments described are intended to explain the best mode known for practicing the invention and to enable others skilled in the art to utilize the invention in such, or other, embodiments and with various modifications required by the particular applications or uses. It is intended that the appended claims be construed to include alternative embodiments to the extent permitted by the prior art.

What is claimed:

1. A recombinant AAV (rAAV) particle produced by a method comprising culturing a cell comprising:
    i) closed ended, linear duplex (CELiD) DNA comprising heterologous DNA; and,
    ii) one or more nucleic acid molecules encoding one or more AAV capsid (Cap) proteins;
    under conditions suitable for formation of AAV particles containing the CELiD DNA, wherein the particle comprises CELiD-derived DNA comprising heterologous DNA and wherein DNA from a source other than an AAV or the heterologous DNA in the CELiD-derived DNA makes up less than 10% of the total amount of DNA in the particle.

2. A kit comprising the rAAV particle of claim 1.

3. A method of eliciting an immune response in an individual, comprising administering the rAAV particle of claim 1 to the individual, wherein the rAAV particle comprises heterologous DNA encoding an immunogenic protein.

4. A recombinant AAV (rAAV) particle comprising closed ended, linear duplex (CELiD)-derived DNA comprising heterologous DNA wherein DNA from a source other than an AAV or the heterologous DNA in the CELiD-derived DNA makes up less than 10% of the total amount of DNA in the particle.

5. The rAAV particle of claim 4, wherein the rAAV particle is produced using a method comprising culturing a cell comprising:
    i) closed ended, linear duplex (CELiD) DNA comprising the heterologous DNA; and,
    ii) one or more nucleic acid molecules encoding one or more AAV capsid (Cap) proteins;
        under conditions suitable for formation of AAV particles containing the CELiD-derived DNA.

6. The rAAV particle of claim 5, wherein the one or more nucleic acid molecules encoding one or more AAV capsid (Cap) proteins is/are stably inserted into the genome of the cell.

7. The rAAV particle of claim 5, wherein the cultured cell comprises one or more polynucleotide molecules encoding one or more AAV Rep proteins, and wherein the culture conditions comprise a culture environment suitable for replication of the CELiD DNA, expression of the one or more Cap proteins, and expression of the one or more Rep proteins.

8. The rAAV particle of claim 5, wherein the cell is an invertebrate cell or a mammalian cell.

9. The rAAV particle of claim 4, wherein the heterologous DNA encodes a protein or a therapeutic RNA.

10. The rAAV particle of claim 9, wherein the therapeutic RNA comprises a siRNA, a RNAi, a shRNA, a miRNA, an aptamer, or a ribozyme.

11. The rAAV particle of claim 1, wherein DNA from a source other than an AAV or the heterologous DNA in the CELiD-derived DNA makes up less than 1% of the total amount of DNA in the particle.

12. The rAAV particle of claim 1, wherein DNA from a source other than an AAV or the heterologous DNA in the CELiD-derived DNA makes up less than 0.1% of the total amount of DNA in the particle.

13. The rAAV particle of claim 1, wherein DNA from a source other than an AAV or the heterologous DNA in the CELiD-derived DNA makes up less than 0.01% of the total amount of DNA in the particle.

14. The rAAV particle of claim 4, wherein DNA from a source other than an AAV or the heterologous DNA in the CELiD-derived DNA makes up less than 1% of the total amount of DNA in the particle.

15. The rAAV particle of claim 4, wherein DNA from a source other than an AAV or the heterologous DNA in the CELiD-derived DNA makes up less than 0.1% of the total amount of DNA in the particle.

16. The rAAV particle of claim 4, wherein DNA from a source other than an AAV or the heterologous DNA in the CELiD-derived DNA makes up less than 0.01% of the total amount of DNA in the particle.

17. The rAAV particle of claim 1, wherein the heterologous DNA encodes a protein or a therapeutic RNA.

18. The rAAV particle of claim 17, wherein the therapeutic RNA comprises a siRNA, a RNAi, a shRNA, a miRNA, an aptamer, or a ribozyme.

19. The rAAV particle of claim 1, wherein the one or more nucleic acid molecules encoding one or more AAV capsid (Cap) proteins is/are stably inserted into the genome of the cell.

20. The rAAV particle of claim 1, wherein the cultured cell comprises one or more polynucleotide molecules encoding one or more AAV Rep proteins, and wherein the culture conditions comprise a culture environment suitable for replication of the CELiD DNA, expression of the one or more Cap proteins, and expression of the one or more Rep proteins.

21. The rAAV particle of claim 1, wherein the cell is an invertebrate cell or a mammalian cell.

22. A method of eliciting an immune response in an individual, comprising administering the rAAV particle of claim 4 to the individual, wherein the rAAV particle comprises heterologous DNA encoding an immunogenic protein.

23. A kit comprising the rAAV particle of claim 4.

* * * * *